United States Patent [19]

Monks et al.

[11] 4,202,876

[45] May 13, 1980

[54] INVESTIGATING BODY FUNCTION

[75] Inventors: Reginald Monks; Anthony L. M. Riley, both of Amersham, England

[73] Assignee: The Radiochemical Centre Limited, England

[21] Appl. No.: 866,853

[22] Filed: Jan. 4, 1978

[30] Foreign Application Priority Data

Jan. 7, 1977 [GB] United Kingdom .................. 628/77

[51] Int. Cl.$^2$ ...................... A61K 29/00; A61K 43/00
[52] U.S. Cl. ..................................... 424/1.5; 250/303; 260/397.2; 424/1; 424/9
[58] Field of Search ............................... 424/1, 1.5, 9; 260/397.2; 250/303

[56] References Cited

U.S. PATENT DOCUMENTS

| 3,784,576 | 1/1974 | Counsell | 424/1 X |
| 3,993,741 | 11/1976 | Otto | 424/1 |
| 4,024,234 | 5/1977 | Monks et al. | 424/1.5 |
| 4,041,145 | 8/1977 | Van der Veek | 424/1 |
| 4,083,947 | 4/1978 | Monks et al. | 424/1 |

Primary Examiner—Benjamin R. Padgett
Assistant Examiner—Christine M. Nucker

[57] ABSTRACT

Body function of a mammal is investigated using a γ-emitting $^{75}$Se or $^{123m}$Te labelled derivative of a bile acid or bile salt. Thus bowel function may be investigated by oral administration of the labelled compound followed, after a suitable period of time, by either a whole body count or a faecal count of radioactivity. Preferred bile acids and salts are substituted either at the 19-position or in the C-17 side chain.

9 Claims, No Drawings

INVESTIGATING BODY FUNCTION

This invention relates to the investigation of body function, especially small bowel function but also liver function, using bile acids and bile salts or their metabolic precursors labelled with radio isotopes of selenium or tellurium.

Bile salts are synthesized in the liver from cholesterol, pass via the hepatic and common bile ducts to the intestinal tract, are reabsorbed in the ileum and return to the liver via the portal venous system. During this enterohepatic circulation in a normal human more than 95 percent of the bile salts entering the small intestine are reabsorbed, the remainder entering the large intestine and eventually appearing in the faeces. Malfunctioning of the ileum, which can be caused by a number of pathological conditions, can result in the deficient absorption of bile salts. A measurement of bile salts absorption by the intestine would therefore provide useful information enabling the distal small bowel to be recognized, or eliminated, as the source of gastrointestinal disorder.

Bile acids may be represented by the following formula:

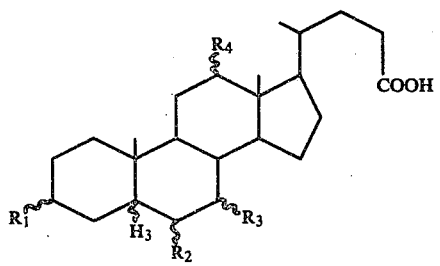

(I)

wherein $R_1$, $R_2$, $R_3$ and $R_4$ are, independently a hydrogen atom or an α- or β-hydroxyl group, and wherein $H_5$ is either in the α or β position.

Bile salts are conjugates of the above bile acids with amino acids, in particular glycine and taurine.

Carboxyl-$^{14}$C-cholic acid (1, $R_2=H$, $R_1=R_3=R_4=\alpha\text{-OH}$; $H_5$ is β) and its taurine conjugate have been used to study the absorption of bile salts in the intestine of both animals and man under a variety of pathological conditions, e.g. regional ileitis, ileal resection, and induced diarrhoea. The investigations have required the measurement of $^{14}$C radioactivity in faeces, urine and bile. In the breath test as devised by Fromm and Hofmann glycine-1-[$^{14}$C]glycocholate is used to detect increased bacterial deconjugation of the bile salts. Upon deconjugation in the small bowel as a result of bacterial overgrowth or in the colon following bile salt malabsorption, the glycine liberated is metabolized, absorbed, and partly exhaled as $^{14}CO_2$. In the case of bile salt malabsorption some of the $^{14}$C radioactivity will appear in the faeces. A faecal $^{14}$C measurement is essential for complete exploitation of the diagnostic scope of the breath test. In the diagnosis of bile acid malabsorption the Schilling test employing labelled cyanocobalamin with intrinsic factor is often helpful, but by itself it cannot discriminate between bacterial overgrowth and ileal dysfunction.

The measurement of bile acid adsorption as a routine test for small bowel function would be greatly facilitated if the bile acids could be labelled with a gamma emitting isotope. Counting of gamma emitters is in general easier and more economical than is counting of beta emitters: this particularly applies to biological samples such as bile or faeces, where for beta emitters it would be necessary to process the sample before counting could begin. Labelling with a gamma emitter would possess the additional advantage of allowing body counting and thus obviate the need to handle faecal samples; visualisation of the enterohepatic system would also be possible. The gamma emitting isotopes which could possibly be employed to label bile acids without changing their biological behaviour, and in which the label would remain attached throughout the enterohepatic cycle, are limited in number. This invention concerns the use of radioisotopes of selenium and tellurium, such as selenium-75 and tellurium-123m, to fulfil the required function. The incorporation of either selenium or tellurium into the structure of the bile acid molecule has so far not been described; this applies to both the radioactive and non-radioactive forms of these elements.

The idea behind this invention arises from the observation that when 19-methyl-[$^{75}$Se]selenocholesterol was administered intravenously to humans with the object of adrenal visualisation the selenium-75 radioactivity became concentrated in the enterohepatic system and that the metabolism of 19-methyl-[$^{75}$Se]selenocholesterol appeared to parallel that of cholesterol. It was surmised that 19-methyl-$^{75}$Se selenocholesterol was being converted to analogues of bile salts in which a methylseleno group was attached to the $C_{19}$ carbon atom.

The present invention provides, in one aspect, a method for investigating body function, especially small bowel function, of a mammal, comprising introducing a γ-emitting radioactive Se or Te labelled derivative of a bile acid or an amino acid conjugate thereof (bile salt) or a metabolic precursor thereof into the live mammal, and after the elapse of a suitable period of time determining the distribution of the radioactivity. For determining small bowel function, the labelled bile acid or bile salt is preferably introduced orally. The distribution of radioactivity may be determined by counting of body radioactivity, e.g. by means of a whole body counter, or by measurement of faecal radiation. Where faecal measurements are used this invention includes the use of a second, non-absorbable, γ-emitting isotope, e.g. $^{131}$I-polyvinylpyrollidone or $^{51}$Cr as a marker. This investigation of body function may involve visualising a part, e.g. the hepatobiliary system, of the mammal, by introducing in the live mammal a γ-emitting radioactive selenium or tellurium derivative of a bile acid or its amino acid conjugate, allowing the labelled bile acid to concentrate in the part, e.g. the hepatobiliary system, and observing the radiation emitted by the labelled bile acid in the said part.

In the case of whole body and faecal determination of Se or Te distribution, measurements cannot commence until after excretion of some of the radioactivity from the body. This would normally be a minimum of about 24 hours after ingestion of the labelled bile salt but could vary with some patients. It is also possible to carry out measurements over an extended period of time, say over 7–14 days, in order to gain more accurate estimates of excretion rates. In the case of plasma determination measurements may be started in less than 24 hours after ingestion of the bile salt since absorption through the intestine into plasma would occur well before elimination of radioactivity via the faeces. Here again it is also possible to carry out measurements over an extended period of time in order to gain more accurate information.

It has recently been shown that the blood level of bile acids and bile salts, determined in vitro by radioimmunoassay, can provide a sensitive indication of liver function. According to the present invention, the introduction of a radioactively labelled bile acid or bile salt into the bloodstream enables this determination to be effected in vivo quickly and simply. For this purpose, the labelled bile acid or bile salt is preferably administered intravenously, and samples of blood taken for radioactive counting after appropriate intervals of time.

When the mammal is an adult human being, the dose administered is generally in the range of 1 to 500 μCi, e.g. from 1 to 50 μCi for investigating organ function or from 50 to 500 μCi for organ visualisation.

Techniques for introducing a bile acid into live mammals and allowing it to become absorbed and localized are known in the art and will not be further described here. Measurement of the γ-radiation emitted by the selenium or tellurium and visualization of the hepatobiliary system or other parts of the mammal where the labelled bile acid is concentrated, can be effected with standard equipment. Equipment for measuring body radioactivity may suitably be a whole body counter, or a γ-camera with the collimator removed which may be pointed at all or just the relevant part of the body.

The labelled bile acids or their salts and their metabolic precursors used in the above method include those shown in formulae (2) and (3) below and which are substituted by either Se or Te either at the C-19 position or in the C-17 side chain of the molecule; also Se or Te labelled derivatives of compounds such as 7α-hydroxy-19-methylselenocholesterol which are intermediate in the metabolic conversion of compounds such as 19-methylselenocholesterol to a 19-methylseleno bile acids or bile salts; also those shown in formula (4) below.

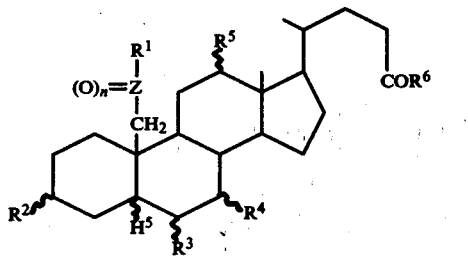

(2)

wherein

Z is a γ-emitting radioactive isotope of selenium or tellurium, $R^1$=alkyl (e.g. $C_1$–$C_4$ alkyl); cycloalkyl (e.g. cyclohexyl); or aralkyl (e.g. benzyl)

$R^2$, $R^3$, $R^4$, and $R^5$ are independently hydrogen or an α- or β-hydroxyl group, $R^6$ is —OH or an amino acid residue $H^5$ may be α-H or β-H n=0 or 1,

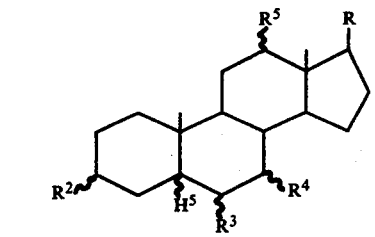

(3)

wherein
R is

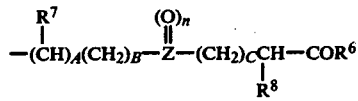

and
A is 0 or 1,
B is 0 to 4,
C is 0 to 4,
Z is a γ-emitting radioactive isotope of selenium or tellurium,
$R^6$ is —OH or an amino acid residue,
$R^7$ is hydrogen or saturated $C_1$ to $C_4$ alkyl group when A is 1,
$R^8$ is hydrogen or saturated $C_1$ to $C_4$ alkyl group,
n is 0 or 1,
$R^2$, $R^3$, $R^4$ and $R^5$ are independently hydrogen or an α- or β-hydroxyl group, or an oxo group,
$H_5$ is an α- or β-H.

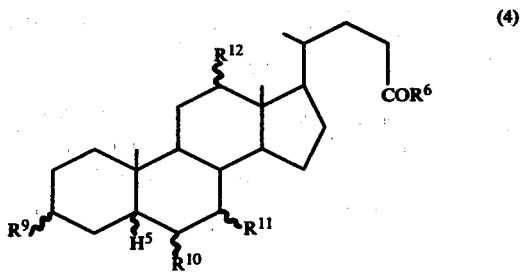

(4)

wherein
$R^6$ is —OH or an amino acid residue.
$R^9$, $R^{10}$, $R^{11}$ and $R^{12}$ are independently a hydrogen atom, an α- or β-hydroxyl group or an α- or β-SeCH$_3$ group, -SeR$^{13}$ where $R^{13}$ is $C_1$ to $C_4$ alkyl, provided that at least one is an α- or β-group -SeR$^{13}$, and
$H_5$ is either in the α- or the β- position.

The present invention provides, in a second aspect, labelled bile acids and their bile salt derivatives substituted by Se or Te at either 19C or in the C-17 side chain and defined by the formula (2) and (3) above respectively.

This invention includes the inactive compounds and also, more particularly, the compounds labelled with radioactive isotopes of selenium and tellurium, e.g. selenium-75 and tellurium-123m. The inactive compounds are useful aids in determining the properties of the radioactive compounds.

The labelled bile acids of the present invention and their amino acid conjugates may be prepared by the following routes:

1. 19-alkylseleno bile acids and their conjugates

The compounds of this group corresponding to formula (2) may be prepared biologically.

19-methyl-[$^{75}$Se]selenocholesterol, or a suitable intermediate on the metabolic pathway of its conversion to a bile salt analogue, e.g. 7α-hydroxy-19-methyl-[$^{75}$Se]-selenocholesterol, is administered intravenously to a suitable animal, e.g. rat or rabbit, with a biliary fistula. The $^{75}$Se compound is converted in the liver of the live animal to a $^{75}$Se-labelled bile salt analogue, which is controlled in the bile via the biliary fistula. Methods of separating and purifying bile acids and their conjugates from samples of bile are known in the art. For example, the bile is added to 20 volumes of absolute ethanol. After brief boiling and subsequent cooling the extract is filtered and evaporated to dryness. The solid residue after extraction with petroleum ether to remove fats, is then dissolved in methanol and the methanolic solution, after filtration to remove inorganic salts, is evaporated to dryness in vacuo to yield a mixture of natural and $^{75}$Se-labelled bile salts. The crude product may be further purified by preparative thin-layer chromatography. The advantage of using an intermediate metabolite such as 7α-hydroxy-19-methyl-[$^{75}$Se]selenocholesterol is that higher yields of the $^{75}$Se bile acids are obtained. An isolated perfused liver may be used as an alternative to using a live animal for the biological preparation of a $^{75}$Se-labelled bile salt.

The above described process has been used to provide analogues of bile salts in which the methyl group attached to the $C_{10}$ carbon atom is replaced by a methyl-selenomethyl group. The products behaved as amino acid conjugates of bile acids both in their chromatographic behaviour and as substrates for the enzyme cholylglycine hydrolase.

2. BILE ACIDS AND THEIR CONJUGATES WITH A SELENIUM ATOM IN THE $C_{17}$ SIDE CHAIN

The compounds of this group, corresponding to formula (3), may be prepared by the reaction of a suitable selenium or tellurium nucleophile with a modified bile acid having a terminal halogen atom, e.g. bromine or iodine, in the $C_{17}$ side chain. These reactions are carried out in such solvents as ethanol, propanol, tetrahydrofuran or dimethylformamide, or mixtures of these solvents, generally at room temperature. The selenium or tellurium nucleophiles are produced by the reaction in liquid ammonia of disodium diselenide or ditelluride with an ω-halogenated carboxylic acid or its ester, the resulting organic diselenide or ditelluride being dissolved in one of the above solvents and cleaved by reagents such as sodium borohydride or dithiothreitol; further reaction with the modified bile acid is effected in situ.

Alternatively, the halogenated bile acid may be reacted with disodium diselenide in a solvent such as propanol at elevated temperatures to provide a disteroidal diselenide. The disteroidal diselenide is dissolved in ethanol, cleaved with sodium borohydride, and the selenol reacted in situ with an ω-halogenated carboxylic acid ester.

The use of potassium selenocyanate affords a useful route to the compounds of this group. Potassium selenocyanate, prepared by dissolving red selenium in ethanolic potassium cyanide, is reacted in ethanol at reduced temperatures with a ω-halogenocarboxylic acid ester. The resulting ω-selenocyanato-carboxylic acid ester is reduced with sodium borohydride and reacted in situ with the halogenated bile acid intermediate. These reactions are usually conducted at room temperature in ethanol or ethanol/tetrahydrofuran mixtures.

ω-Halogenated carboxylic acid esters may be used in place of ω-halogenated compounds in the above reaction to provide products having a side chain in the α-position to the carboxyl group.

Where hydroxyl groups have been protected by acylation and carboxylic acid groups by esterification the protecting groups are removed by standard methods prior to final purification of the product by preparative layer chromatography on silica gel.

The bile acid analogues, containing either a selenium or a tellurium atom in the $C_{17}$ side chain, may be conjugated via an amide linkage to amino acids such as glycine and taurine. The methods used to prepare the bile acid conjugates are well known in the art and depend on the condensation of the bile acid with the amino acid in a suitable solvent such as dimethylformamide and in the presence of a condensing agent such as a carbodiimide or N-ethoxy-carbonyl-2-ethoxy-dihydroquinoline (EEDQ).

The reaction schemes below illustrate the preparations broadly described above. Further detail is provided in the Examples. It is to be understood that these preparations may be carried out with either natural selenium or tellurium or with these elements enriched with their respective radioactive isotopes, e.g. $^{75}$Se or $^{123m}$Te.

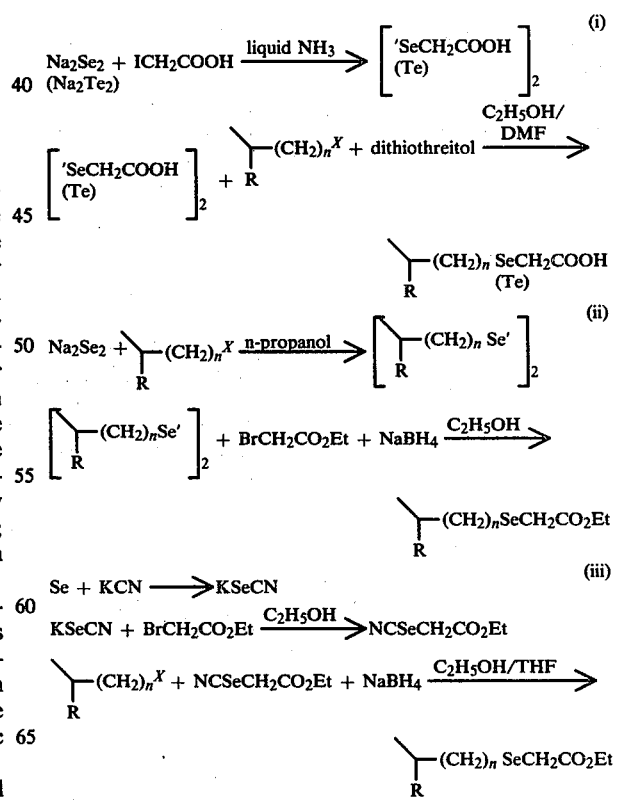

N.B.
R=bile acid nucleus
X=halogen

The insertion of either a selenium or tellurium atom into the $C_{17}$ side chain of a bile acid according to formula (3) is dependent upon the availability of modified bile acid intermediates having a terminal halogen atom, e.g. bromine or iodine, in the $C_{17}$ side chain. The provision of such intermediates has required the shortening or lengthening of the $C_{17}$ side chain by methods known in the art, e.g. Barbier-Wieland degradation or the Arndt-Eistert reaction respectively. Replacement of the terminal carboxyl group by a halogen atom may be effected by the Hunsdiecker reaction. A particularly effective means of accomplishing this replacement is to treat the bile acid in refluxing carbon tetrachloride with lead tetra-acetate/iodine reagent, the reaction mixture being irradiated with light meanwhile. The hydroxyl groups of the bile acid must be protected with suitable groups such as formyl, acetyl, nitro, etc. This reaction results in the replacement of the carboxyl group with an iodine atom. The degradation of the $C_{17}$ side chain of cholic acid to provide a 20-iodo-5$\beta$-pregnane derivative may be effected by three consecutive reactions:

(1) refluxing of the protected bile acid in dry benzene and under nitrogen with lead tetraacetate in the presence of cupric acetate and pyridine provides a corresponding $\Delta^{22}$-24-nor-5$\beta$-cholene, (A);

(2) treatment of A with sodium periodate/potassium permanganate in aqueous 2-methylpropan-2-ol in presence of potassium carbonate causes oxidation of the $\Delta^{22}$ bond and provides the 3$\alpha$,7$\alpha$,12$\alpha$-triformoxy-23,24-bisnor-5$\beta$-cholanic acid, (B);

(3) B is refluxed in carbon tetrachloride with lead tetraacetate/iodine reagent under light irradiation to provide the 3$\alpha$,7$\alpha$,12$\alpha$-triformoxy-20-iodo-5$\beta$-pregnane derivative, (C). C is probably a mixture of R and S isomers but the proportions have not been determined.

The above reaction can be performed equally using steroids in the 5$\alpha$- or the 5$\beta$- configuration. Available steroids in the 5$\alpha$- configuration include 5$\alpha$-cholanic acid-3$\beta$-ol and 22,23-bisnor-5$\alpha$-cholanic acid-3$\beta$-ol.

3. BILE ACIDS WITH RING SELENOALKYL SUBSTITUTION

The compounds of this group, corresponding to formula (4) may be prepared from the corresponding ring-OH substituted compound by first replacing hydroxyl by iodine and then replacing iodine by selenoalkyl in known manner.

By means which are described in general terms above and in detail in the preparative Examples below, the following ten compounds were prepared:

COMPOUNDS PREPARED (DEFINITIVE NOMENCLATURE)

(i) 19-methyl-[$^{75}$Se]seleno bile salts prepared biosynthetically from 19-methyl-[$^{75}$Se]selenocholesterol.
(ii) 3$\alpha$,12$\alpha$-dihydroxy-22-(carboxymethyl-[$^{75}$Se]seleno)-23,24-bisnor-5$\beta$-cholane
(23-[$^{75}$Se]seleno-25-homodeoxycholic acid)
(iii) 3$\alpha$,7$\alpha$-dihydroxy-23-($\beta$-carboxyethyl-[$^{75}$Se]seleno)-24-nor-5$\beta$-cholane
(iv) 3$\alpha$,7$\alpha$,12$\alpha$-trihydroxy-23-($\beta$-carboxyethyl-[$^{75}$Se]seleno)-24-nor-5$\beta$-cholane
(v) 3$\alpha$,7$\alpha$,12$\alpha$-trihydroxy-20-(carboxymethyl-[$^{75}$Se]seleno)-5$\beta$-pregnane
(22-[$^{75}$Se]selenacholic acid)
(vi) Glyco-22-[$^{75}$Se]selenacholic acid
(Glycine conjugate of v)
(vii) 3$\alpha$-hydroxy-24-(carboxymethyl-[$^{75}$Se]seleno)-5$\beta$-cholane
(viii) 3$\alpha$,12$\alpha$-dihydroxy-23-(carboxymethyl-[$^{123m}$Te]telluro)-24-nor-5$\beta$-cholane
(ix) Tauro-23-[$^{75}$Se]selena-25-homodeoxycholic acid
(Taurine conjugate of ii)
(x) 3,7,12-triketo-23-(carboxymethyl-[$^{75}$Se]seleno)-24-nor-5$\beta$-cholane.

N.B. When selenium and tellurium are used as part of a prefix e.g. carboxymethylseleno, the words used are seleno and telluro. Selena and tellura are used to denote replacement of a $CH_2$ group e.g. 22-selenacholic acid denotes replacement of the $C_{22}$ carbon atom by Se.

BIOLOGICAL EVALUATION

A. Tissue Distribution Studies

Tissue distribution studies in rats, after oral administration of compounds i to viii, show that these compounds are excreted in the faeces to an extent greater than 90 percent after a period of 7–8 days. The pattern of tissue distribution is similar for all the compounds. At 20 hours the $^{75}$Se radioactivity is largely confined to the liver, gut and faeces; apart from compounds iii and iv less than 5 percent of the radioactivity is distributed among other organs. Compound ii at this time exhibits a somewhat different behaviour in that it shows a very much small percentage of $^{75}$Se radioactivity in the faeces and a correspondingly larger proportion in the small bowel.

B. Whole-Body Excretion Studies

Whole-body excretion studies in rats over a period of 8 days after oral administration of compounds i to viii indicate that excretion is delayed with respect to a non-absorbable radioactive maker, $^{131}$I-polyvinylpyrrolidone.

For each of the eight compounds under investigation, approximately 10–15 $\mu$Ci was administered via an intragastric tube to rats. Whole-body counts were determined immediately after administration and at intervals during the following 6–8 days. A whole-body standard permitted corrections for radioactive decay and variations in counter efficiency.

Whole-body retention is expressed as a percentage of the counts determined immediately after administration.

Graphical analysis of the results revealed that, in every case, the data could be approximated by a function of the form:

$$\text{Retention } (t) = ae^{-xt} + be^{-yt} + c \qquad (1)$$

The values obtained for each of the parameters in equation 1 for each of the substances are tabulated below.

|      | a(%) | x(d$^{-1}$) | b(%) | y(d$^{-1}$) | c(%) |
|------|------|-------------|------|-------------|------|
| ii   | 190  | 2.29        | 27.6 | 0.65        | 3.36 |
| iv   | 260  | 2.77        | 42.5 | 0.66        | 15.5* |
| iii  | 170  | 2.31        | 37.5 | 0.53        | 4.0  |
| v    | 98   | 2.52        | 16.5 | 0.38        | 0.8  |
| vi   | 221  | 1.54        | 7.2  | 0.54        | 0.58 |
| vii  | 203  | 2.29        | 11.8 | 0.44        | 2.85 |
| i    | 80   | 2.02        | 7.1  | 0.62        | 6.0  |
| viii | 173  | 2.26        | 6.3  | 0.43        | 1.3  |

*Probably closer to 5.5% as revealed by dissecton results.

The first component (ae$^{-xt}$) is variable. A consistent pattern emerges however. The half-life of this first component ranged from 0.25 to 0.45 days. The half-life of the non-absorbed gastrointestinal marker, I$^{131}$ P.V.P. has been shown to be approximately 0.17 days, and thus the first component of the bile salt excretion does not represent material that has passed unabsorbed through the alimentary canal. It may however represent that portion of the administered bile salt that after absorption, is metabolised on its first pass through the liver, and is not reabsorbed.

The second component (be$^{-yt}$) had a half-life in the range 1.05 to 1.82 days. This is approximately 10 times the half-life of a non-absorbed marker and certainly represents material that has been absorbed from the gastrointestinal tract. This material is probably incorporated into the enterohepatic circulation.

The constant (c) represents that percentage of the administered substance that is predicted mathematically as never being excreted (or excreted with a very long half-life compared to those of the other components). The figure for the tri-hydroxy compound is anomalous—tissue distribution studies at the end of 8 days indicated a whole body retention of approximately 5.5%.

C. Biliary Excretion Studies

The biliary excretion from rats of $^{14}$C/$^{75}$Se radioactivity after oral administration of a mixture of a $^{75}$Se-seleno bile acid and $^{14}$C-cholic acid provides information not revealed in the previous studies. The $^{14}$C-cholic acid acts as an internal comparison marker for each rat studied. Measurement of the ratio of the $^{14}$C/$^{75}$Se radioactivity collected in a 24 hour bile sample to the $^{14}$C/$^{75}$Se radioactivity administered orally gives an indication of the efficiency of absorption of the seleno bile acid as compared to $^{14}$C-cholic acid. Ideally, when these absorptions are the same the ratio would be 1, but as the efficiency of the adsorption seleno bile acid diminishes the ratio increases. In the compounds studied the ratio for i,ii and v ranges from 3 to 5, whereas for iii it is 54 which indicates a very much reduced absorption. In the case of compounds i, ii and v the pattern of appearance of $^{75}$Se radioactivity in the bile is similar to that of the $^{14}$C radioactivity. This similarity, which is not shown by compound iii, indicates the same site of absorption for both the seleno bile acid and cholic acid.

D. Clinical Use

It has been shown by whole-body counting that in normal humans having no past history of bowel dysfunction the rate of elimination of $^{75}$Se-ii from the body is considerably slower than it is for rats. However, in humans who have suffered on ileal resection this rate of elimination is increased.

These $^{75}$Se-seleno bile acids may therefore be used to investigate malabsorption of bile acids associated with ileal dysfunction. Measurement of rate of excretion may be performed either by whole-body counting or by faecal counting utilising a γ-scintillation counter.

CLINICAL EXAMPLES

Approximately 1 μCi of compound ii was given orally as a drink in water to four adult volunteers, two of them being normal active adult males, 35–50 years of age, and two who had received a total ileal resection more than 10 years previously. All were on a normal diet. Se-ii was administered between 10.00 am and 12 noon. Body radioactivity was then measured in a whole-body counter immediately after administering the $^{75}$Se-ii and subsequently at 48 hours and 7 days.

RESULTS

| | Retention of Selenium-75 Radioactivity at | | |
|---|---|---|---|
| | 0 | 48 hrs. | 7 days |
| Normal (1) | 100% | 80% | 31% |
| Normal (2) | 100% | 100% | 27% |
| Ileal resection (3) | 100% | 26% | 7.5% |
| Ileal resection (4) | 100% | 80% | 9.5% |

Patient (4) was an old inactive female who was on drugs to slow down bowel transfer.

The difference in retained radioactivity between normal patients (1) and (2) and ileal resection patients (3) and (4) is large enough to be readily observed. The method offers the following advantages over the use of carbon-14 labelled bile sal salts:

(a) Bowel function can be investigated by body counting of γ-radiation, without the need for faecal counting or for preparation of samples for counting β-radiation.

(b) Because only small amounts of labelled bile salts are used, and because these are rapidly eliminated, the patient is subjected to only low levels of radiation.

The labelled compounds might conveniently have been administered in the form of a capsule containing the labelled bile salt adsorbed on a carrier.

The following preparative Examples further illustrate the invention.

EXAMPLE 1

The Preparation of a mixture of 19-methyl-$^{75}$Se seleno-labelled bile salts

A male rabbit (NZW×LOP; 4.8 kg) was anaesthetized with sodium pentobarbitone ("Sagatal"), intravenously injected. A tracheotomy was performed and into a jugular vein was inserted a cannula with a 3-way tap. The animal was ventilated by intermittent positive pressure and anaesthesia maintained by intravenous administration of pentobarbitone as required. A midline ventral incision was made in the abdominal wall and the liver reflected to reveal the gall bladder, cystic duct and the common bile duct. After ligation of the cystic duct the common bile duct was cannulated for the collection of bile.

After a period of stabilization 1 ml of a solution of 19-methyl-[$^{75}$Se]selenocholesterol (0.01 mg; 12 mCi) in polysorbate/normal saline was injected via the jugular cannula. Bile was collected as a series of 15-minute samples in preweighed tubes. After collection each sample was weighed and counted for $^{75}$Se radioactivity. The flow of bile, initially at 3.4 ml/15 minutes, declined to 1.5 ml/15 minutes after 6½ hours. During this period 56.65 g of bile was collected containing approximately 100 μCi of $^{75}$Se radioactivity (about 1 percent of the injected dose).

The labelled bile was added to 1000 ml of absolute ethanol which was vigorously stirred and brought momentarily to boiling. The ethanolic solution, after cooling, was filtered and reduced in volume to 10 ml. A small precipitate at this stage was again removed by filtration, and the filtrate was evaporated to dryness in vacuo. The residual green gum was extracted with 40°–60° petroleum ether (4×5 ml) to remove lipid material, and then dissolved in methanol (2×5 ml) and the solution filtered. Yield of $^{75}$Se bile salts, 60 μCi. TLC: Kieselgel 60 F$_{254}$; chloroform, methanol 5:1 major component (>90%) R$_f$ 0.00 (Inactive markers of glycocholic acid, R$_f$ 0.00; glycocheno-deoxycholic acid, R$_f$ 0.06; cholic acid, R$_f$ 0.14; deoxycholic acid, R$_f$ 0.70.)

The methanolic solution, containing both natural bile salts and $^{75}$Se labelled bile salts, was reduced in volume and applied to six PLC plates. (Kieselgel 60 F$_{254}$, 2 mm). The plates were eluted with chloroform, methanol (5:1), autoradiographed, and the component at R$_f$ 0.00 removed from the plates and extracted into methanol. Yield, 26 μCi. On treatment of a sample of this purified 19-methyl-[$^{75}$Se]seleno labelled bile salt with the enzyme cholylglycine hydrolase the chromatographic mobility on Merck Kieselgel 60 F$_{254}$ (chloroform, methanol 5:1) changed from R$_f$ 0.00 to R$_f$s 0.30 and 0.47).

EXAMPLE 2

The Preparation of
3α,12α-dihydroxy-22-(carboxymethyl-[$^{75}$Se]seleno)-23,24-bisnor-5β-cholane (23-Selena-25-homodeoxycholic Acid)

(i) 3α,12α-Diacetory-22-Iodo-23,24-bisnor-5β-cholane

3α,12α-Diacetoxy-24-nor-5β-cholanic acid (0.3 g) in dry carbon tetrachloride (30 ml) was treated with dry, powdered, lead tetraacetate (0.3 g) and was heated to reflux in an atmosphere of dry nitrogen. The solution was irradiated with an Atlas 275 watt infra-red lamp and a solution of iodine (0.16 g) in dry carbon tetrachloride (12 ml) was added portionwise over a period of 10 minutes. The reaction mixture was irradiated and stirred for a further 1 hour and was allowed to cool. The solution was filtered, the filtrate was washed successively with 5% sodium thiosulphate solution and water, and then dried over anhydrous sodium sulphate. Evaporation of the solvent and crystallisation of the residue from ethanol gave 3α,12α-diacetoxy-22-iodo-23,24-bisnor-5β-cholane (0.3 g, 85%) m.p. 172°–174°.

TLC (Merck Kieselgel 60 F$_{254}$; chloroform): Single component Rf0.50.

IR Spectrum: $\bar{v}$ max: 2960, 2930, 2870, 1735, 1453, 1374, 1239, 1194, 1018 cm$^{-1}$.

NMR (220 MH$_z$, CDCl$_3$): τ 4.95 (1H,S,C$_{12}$-proton); τ 5.32 (1H,M,C$_3$-proton); τ 6.76 (2H,M,C$_{22}$—H), τ 7.86 (3H,S,12-Acetate protons), τ 7.98 (3H,S,3-acetate protons), τ 8.00–9.05 (22H, steroid nucleus), τ 9.10 (6H,S (with minor splitting), C$_{19}$—H+C$_{21}$—H), τ 9.23 (3H,S,C$_{18}$—H).

(ii) 23-Selena-25-homodeoxycholic acid-$^{75}$Se

Red selenium-$^{75}$Se was precipitated by bubbling sulphur dioxide through a solution of sodium selenite (15.9 mg) in water (2 ml) and concentrated hydrochloric acid (4 ml) containing sodium selenite-$^{75}$Se (11.7 mCi, 1.2 mg selenium). The precipitate was centrifuged off, it was washed thoroughly with de-ionised water and dried over phosphorus pentoxide under vacuum.

Red selenium-$^{75}$Se (8.4 mg, 0.11 mA, 109 mCi/mA) was suspended in ethanol (2 ml) and potassium cyanide (7 mg, 0.11 mmole) was added; the mixture was stirred at room temperature for two hours until complete solution had occurred. Redistilled ethyl bromoacetate (12 μl) was added to the solution at 0° C. and it was stirred for 1½ hours. 3α,12α-Diacetoxy-22-iodo-23,24-bisnor-5β-cholane (60 mg) in dry tetrahydrofuran (1 ml) was added to sodium borohydride (9 mg) in ethanol (1 ml). The reaction mixture was cooled in ice and the ethanolic solution of ethyl selenocyanatoacetate-$^{75}$Se was added over a period of 10 minutes. Stirring was continued for a further 2 hours while the temperature rose to room temperature. Acetone (1 ml) was added and the solution was evaporated under reduced pressure. Chloroform (2 ml) was added to the residue, insoluble material was removed by filtration and the solution was concentrated to a small bulk. The required product was isolated by preparative layer chromatography (Anachem Silica Gel GF, 1 mm; chloroform, methanol 20:1). The major component, Rf0.85, as observed by autoradiography, was removed from the plate and extracted into ethyl acetate (3×4 ml). Yield of ethyl 3α,12α-diacetoxy-23-selena-25-homo-5β-cholanate-$^{75}$Se, 6.1 mCi.

IR Spectrum: $\bar{v}$ max: 2935, 2860, 1735, 1450, 1378, 1245, 1050, 750 cm$^{-1}$.

The solution was evaporated and sodium hydroxide (100 mg) in ethanol (5 ml) and water (1 ml) was added. The solution was stirred and heated under reflux for 2 hours; it was then cooled and evaporated. Water (3 ml) was added, the solution was filtered from some insoluble material and acidified by the addition of Bio-Rad AG 50W-X12 cation exchange resin in the H+ form. The resin was removed by filtration, it was washed with methanol (3 ml) and the combined filtrate was evaporated. The residue was dissolved in the minimum of methanol and the product was isolated by preparative layer chromatography (Anachem Silica Gel GF, 1 mm; chloroform, methanol 6:1). The required band, Rf0.42, was located by autoradiography; it was removed from the plate and isolated by extraction into methanol. Evaporation of the solvent afforded 23-selena-25-homodeoxycholic acid-$^{75}$Se(2.4 mCi).

TLC (Merck Kieselgel 60 F$_{254}$):
(a) Chloroform, methanol-5:1; Major component (95%) Rf0.36
(b) Iso octane, diisopropyl ether, acetic acid-2:1:1; Major component Rf0.43

IR Spectrum: $\bar{v}$ max: 3380, 2930, 2860, 1700, 1448, 1380, 1255, 1105, 1035 cm$^{-1}$.

(iii) Tauro-23-selena-25-homodeoxycholic acid-$^{75}$Se

23-Selena-25-homodeoxycholic acid-$^{75}$Se (0.27 mCi, 2.0 mg) was treated with a solution of N-ethoxycarbonyl-2-ethoxy-dihydroquinoline (3 mg) in dry dimethylformamide (620 μl) and stirred for 30 minutes. The solution was added to a mixture of taurine (1.55 mg) in dimethylformamide (350 μl) containing triethylamine (3.3 μl) and the reaction mixture was heated at ca. 90° for 30 minutes. After standing at ambient temperature overnight, water (1 ml) was added, the solution was acidified by addition of concentrated hydrochloric acid and evaporated. Ethanol (0.5 ml) was added to the residue and the product was isolated by preparative layer chromatography (Anachem Silica Gel GF, 1 mm; chloroform, methanol-5:2). The product band, Rf0.32, was removed from the plate and the product was isolated by extraction with methanol. Evaporation of the solvent gave tauro-23-selena-25-homodeoxycholic acid-$^{75}$Se (0.14 mCi).

TLC (Merck Kieselgel 60 F$_{254}$; chloroform, methanol 3:1): Major Component (94%) Rf0.34 (cf 23-selena-25-homodeoxycholic acid-Rf 0.65 in the same system).

IR Spectrum: $\bar{v}$ max: 3400, 2940, 2870, 1698, 1650, 1545, 1390, 1208, 1180, 1070 cm$^{-1}$.

(iv) Ethyl 3α,12α-Diacetoxy-23-Selena-25-homo-5β-cholanate and 23-Selena-25-homodeoxycholic Acid Non-radioactive ethyl 3α,12α-diacetoxy-23-selena-25-homo-5β-cholanate and 23-selena-25-homodeoxycholic acid were prepared by the method described in 2(ii). Quantities of reagents used:- ethyl selenocyanatoacetate, 35 mg in 0.7 ml ethanol; sodium borohydride, 12.6 mg; 3α,12α-diacetoxy-23-iodo-23,24-bisnor-5β-cholane, 100 mg; ethanol, 5 ml; tetrahydrofuran, 1 ml. Yield of ethyl 3α,12α-diacetoxy-23-selena-25-homo-5β-cholanate 64 mg.

IR Spectrum: $\bar{v}$ max: 2940, 2865, 1738, 1450, 1380, 1245, 1105, 1060, cm$^{-1}$.

NMR (220 MHz, CDCl$_3$): τ 4.93 (1H,S,C$_{12}$-proton), τ 5.32 (1H,M,C$_3$-proton), τ 5.84 (2H,q,ethyl CH$_2$), τ 6.90 (2H,S,C$_{24}$-protons), τ 7.06 (1H,M,C$_{22}$-proton), τ 7.45 (1H,q,C$_{22}$-proton), τ 7.90 (3H,S,12-acetate protons), τ 7.96 (3H,S,3-acetate protons), τ 8.72 (3H,t,ethyl CH$_3$), τ 9.08 (3H,d,C$_{21}$-protons), τ 9.12 (3H,S,C$_{19}$-protons), τ 9.25 (3H,S,C$_{18}$-protons), τ 8.0–9.25 (22H, steroid nucleus).

Ethyl 3α,12α-diacetoxy-23-selena-25-homo-5β-cholanate (120 mg) was dissolved in ethanol (5 ml) and hydrolysed as described in 2 (ii) giving 23-selena-25-homodeoxycholic acid (45 mg).

TLC (Merck Kieselgel 60 F$_{254}$; chloroform, methanol 5:1): The product, visualised by exposure to iodine vapour, chromatographed as a single component (Rf 0.32) and coincided with the radioactive marker.

IR Spectrum: $\bar{v}$ max: 3430, 2920, 2855, 1700, 1448, 1375, 1255, 1038 cm$^{-1}$.

NMR (220 MHz, CD$_3$OD): τ 5.12 (solvent peak), τ 6.05 (1H,S,C$_{12}$-proton), τ 6.50 (1H,m,C$_3$-proton), τ 6.7 (solvent peak), τ 6.93 (2H,S,C$_{24}$-protons), τ 7.07 (1H,m,C$_{22}$-proton), τ 7.54 (1H,q,C$_{22}$-proton), τ 7.85 (3H,S,CH$_3$CO$_2$H), τ 8.88 (3H,d,C$_{21}$-protons), τ 9.07 (3H,S,C$_{19}$-protons), τ 9.28 (3H,S,C$_{18}$-protons), τ 8.0–9.2 (22H,steroid nucleus).

(v) 23-Selena-25-homodeoxycholic acid selenoxide-$^{75}$Se

23-Selena-25-homodeoxycholic acid-$^{75}$Se [68.4 μCi, 1.1 μmole] in methanol (1.0 ml) was treated with an aqueous solution of hydrogen peroxide (5 μl, 4 μmole) and was allowed to stand at ambient temperature for 90 minutes.

TLC (Merck Kieselgel 60 F$_{254}$, dichloromethane, acetone, acetic acid-7/2/1): Major Component (greater than 90%) Rf 0.19 (cf 23-Selena-25-homodeoxycholic acid-$^{75}$Se Rf 0.84 in this system).

EXAMPLE 3

Preparation of 3α,7α-Dihydroxy-23-(β-carboxyethylseleno)-24-nor-5β-cholane (i) 3α,7α-Dihydroxy-23-(β-carboxyethylseleno)-24-nor-5β-cholane-3,7-dinitrate-$^{75}$Se Red selenium-$^{75}$Se (5.0 mg, 6.4 mCi) was prepared as described in Example 2 (ii) and was suspended in de-ionised water (0.55 ml). Potassium cyanide (4 mg) was added and the mixture was stirred until all the selenium had dissolved. β-Propiolactone (5 μl) was added and after stirring for 15 minutes the solution was acidified by the dropwise addition of concentrated hydrochloric acid (some red selenium was precipitated) and evaporated. Ether (3 ml) was added to the residue and the solution of β-selenocyanatopropionic acid-$^{75}$Se was filtered to remove insoluble products and evaporated (5.4 mCi).

3α,7α-Dihdroxy-23-bromo-24-nor-5β-cholane-3,7-dinitrate (30.8 mg) was dissolved in tetrahydrofuran (1.0 ml) and was added to sodium borohydride (8.3 mg) in ethanol (0.7 ml). The solution was cooled in ice and β-selenocyanatopropionic acid-$^{75}$Se in ethanol (1.0 ml) was added in portions over 10 minutes. After a further 1 hour, acetone (1 ml) was added, the solution was acidified with concentrated hydrochloric acid and evaporated to dryness. The residue was extracted into ether and the solution was filtered from insoluble material. TLC (Merck Kieselgel 60 F$_{254}$; chloroform, methanol 10:1) demonstrated three major radioactive products Rf 0.97, 0.85 and 0.09. Component Rf 0.85 corresponded to inactive marker (Example 3 (iii)).

The product was isolated by preparative layer chromatography (Anachem Silica Gel GF, 1 mm; chloroform; methanol - 10:1). It was located by autoradiography (Rf 0.41). removed from the plate and extracted into ether (3×3 ml) giving 1.1 mCi of 3α,7α-dihydroxy-23-(β-carboxyethylseleno)-24-nor-5β-cholane-3,7-dinitrate.

TLC (Merck Kieselgel 60 F$_{254}$; chloroform, methanol 10:1): Major component (95%) Rf 0.54 corresponds to non-radioactive standard.

(ii) 3α,7α-Dihydroxy-23-(β-carboxyethylseleno)-24-nor-5β-cholane-$^{75}$Se

The dinitrate (1.1 mCi - prepared as described above - 3 (i)) was dissolved in glacial acetic acid (1 ml) and zinc dust (60 mg) was added in portions. The reaction mixture was stirred at ambient temperature for 1 hour and stored at −20° C. overnight. After warming to room temperature the solution was filtered and the filtrate was lyophilized. The product was isolated by preparative layer chromatography (Anachem Silica Gel GF, 1 mm; chloroform, methanol (7:1). It was located by autoradiography (Rf 0.30), removed from the plate and extracted into methanol to give 3α,7α-dihydroxy-23-(β-carboxyethylseleno)-24-nor-5β-cholane (0.6 mCi.

TLC (Merck Kieselgel 60 F$_{254}$):
 (a) chloroform methanol, 5:1; major component (97%) Rf 0.65
 (b) chloroform, methanol; 10:1; major component Rf 0.22
 (c) isooctane, diisopropylether, acetic acid; 2:1:1; major component Rf 0.41

In each case the product coincided with the non-radioactive standard.

(iii) 3α,7α-Dihydroxy-23-(β-carboxyethylseleno)-24-nor-5β-cholane-3,7-dinitrate

Non-radioactive 3α,7α-dihydroxy-23-(β-carboxyethylseleno)-24-nor-5β-cholane was prepared by the method described in (3(i)) using the quantities of reagents as follows: 3α,7α-dihydroxy-23-bromo-24-nor-5β-cholane-3,7-dinitrate (173.1 mg) in tetrahydrofuran (4 ml); sodium borohydride (45.8 mg) in ethanol (2.2 ml) and β-selenocyanatopropionic acid (61.4 mg) in ethanol (2.2 ml). The reaction mixture was treated with acetone (1 ml), it was poured into water (25 ml), acidified with concentrated hydrochloric acid and extracted with ether (2×20 ml). The combined ether extracts were washed with 5% sodium carbonate solution (2×20 ml)

and the combined alkaline extracts were acidified. The precipitate was isolated by ether, the extracts were dried and evaporated. The product was purified by preparative layer chromatography (Merck Kieselgel F$_{254}$, 2 mm—chloroform, methanol (10:1). The required band was located under u.v., it was removed from the plate and extracted into ether. Evaporation of the solvents left 3α,7α-dihydroxy-23-(β-carboxyethylseleno)-24-nor-5β-cholane-3,7-dinitrate as a white solid (82 mg).

IR Spectrum: $\bar{v}$ max: 3450, 2940, 1710, 1620, 1278, 862 cm$^{-1}$.

NMR (220 MHz, CDCl$_3$): τ 4.95 (1H, S C$_7$-proton), τ 5.22 (1H, m, C$_3$ proton), τ 7.23 (4H, S, C$_{25}$ and C$_{26}$-protons), τ 7.6 (2H, m, C$_{23}$-protons), τ 9.05 (6H, s+d, C$_{19}$-protons and C$_{21}$-protons), τ 9.32 (3H, S, C$_{18}$-protons), τ 7.85–9.10 (24H, steroid nucleus).

(iv) 3α,7α-Dihydroxy-23-(β-carboxyethylseleno)-24-nor-5β-cholane

3α,7α-Dihydroxy-23-(β-carboxyethylseleno)-24-nor-5β-cholane (50 mg) was prepared from its dinitrate ester (80 mg) by the method described (3(ii)).

IR Spectrum: $\bar{v}$ max: 3435, 2940, 2870, 1715, 1550, 1410, 1300, 1080, 960 cm$^{-1}$.

NMR (220 MHz, CD$_3$OD): τ 5.16 (solvent peak), τ 6.20 (1H, S, C$_7$-proton), τ 6.94 (1H, m, C$_3$-proton), τ 6.99 (solvent peak), τ 7.25 (4H, S, C$_{25}$ and C$_{26}$-protons), τ 7.45 (2H, m, C$_{23}$ protons), τ 9.02 (3H, d, C$_{21}$-protons), τ 9.07 (3H, S, C$_{19}$-protons), τ 9.29 (3H, S, C$_{18}$-protons).

EXAMPLE 4

Preparation of 3α,7α,12α-Trihydroxy-23-(β-carboxyethylseleno)-24-nor-5β-cholane (i) Cholic Acid Triformate Cholic acid (50 g) was treated with 100% formic acid (240 ml) and the whole was stirred at 70°–80° C. for 6 hours. The solution was cooled and most of the solvent was evaporated. The residue was triturated with ether (500 ml) giving a white solid which was filtered and dried (43 g). The crude product could be further purified by successive recrystallisation from 60% aqueous ethanol and 1:1 60°–80° petrol, acetone. M.p. of purified material 204°–208° C.

(ii) 3α,7α,12α-Triformoxy-23-Iodo-24-nor-5βcholane

Cholic acid triformate (1.06 g) and lead tetracetate (0.97 g) were suspended in dry carbon tetrachloride (100 ml) and the suspension was stirred and heated to reflux in an atmosphere of dry nitrogen. Reflux was maintained by irradiation with an Atlas 275 watt infrared lamp and a solution of iodine (0.52 g) in carbon tetrachloride (40 ml) was added in portions. Reflux was continued for a further 1 hour. The reaction mixture was allowed to cool and then filtered.

The filtrate was washed successively with 5% sodium thiosulphate solution and water, and was dried over anhydrous sodium sulphate. Evaporation of the solvent and recrystallisation of the residue from ethanol (twice) gave 3α,7α,12α-triformoxy-23-iodo-24-nor-5β-cholane (0.65 g) as colourless crystals, m.p. 166°–168°.

IR Spectrum: $\bar{v}$ max: 2960, 2938, 2862, 2712, 1721, 1518, 1360, 1160, 1060, 995, 600 cm$^{-1}$.

NMR (220 MHz, CDCl$_3$): τ 1.85, 1.90, 1.98 (3H, 3 singlets, 3-7-and 12-formate protons), τ 4.74 (1H, S, C$_{12}$-proton), τ 4.94 (1H, S, C$_7$-protons), τ 5.30 (1H, m, C$_3$-proton), τ 6.72+6.95 (2H, m, C$_{23}$ protons), τ 9.06 (3H, S, C$_{19}$-protons), τ 9.15 (3H, d, C$_{21}$-protons), τ 9.22 (3H, S, C$_{18}$-protons), τ 7.8–9.05 (22H, steroid nucleus).

(iii) 3α,7α,12α-Trihydroxy-23-(β-carboxyethylseleno)-24-nor-5β-cholane-$^{75}$Se β-Selenocyanatopropionic acid-$^{75}$Se (4.42 mCi. 108 mCi/mmole) was prepared from red selenium-$^{75}$Se as described for Example 3(i). 3α,7α,12α-Triformoxy-23-iodo-24-nor-5β-cholane (23 mg) in tetrahydrofuran (0.5 ml) was added to Sodium borohydride (5.5 mg) in ethanol (0.5 ml) and the solution was cooled in ice. β-Selenocyanatopropionic acid-$^{75}$Se (4.42 mCi) in ethanol (0.8 ml) was added to the solution over a period of 10 minutes and stirring was allowed to continue for 1 hour. The reaction mixture was treated with acetone (1 ml), acidified with concentrated hydrochloric acid, and evaporated. The residue was partitioned between ether and water and the ethereal phase was separated and extracted with 5% aqueous sodium carbonate solution. The alkaline extract was acidified and the precipitate was isolated by ether extraction.

Ethanol (2 ml), water (0.75 ml) and potassium hydroxide (100 mg) was added to the crude sample of 3α,7α,12α-triformoxy-23-(β-carboxyethylseleno)-24-nor-5β-cholane. The solution was stirred at ambient temperature for 2 hours, it was then acidified and evaporated. Methanol (2 ml) was added to the residue, the solution was filtered from insoluble material and concentrated to small bulk. The product was purified by preparative layer chromatography (Merck Kieselgel 60 F$_{254}$ 1 mm; chloroform, methanol 5:1). The required band was located by autoradiography (Rf 0.35); it was removed from the plate and extracted into methanol to give 3α,7α,12α-trihydroxy-23-(β-carboxyethylseleno)-24-nor-5β-cholane-$^{75}$Se (1.2 mCi).

TLC (Merck Kieselgel 60 F$_{254}$:
(a) chloroform, methanol 5:1—major component (95%) Rf 0.57 corresponded to non-radioactive standard
(b) isooctane, diisopropylether, acetic acid 2:1:1; Rf 0.21

IR Spectrum: $\bar{v}$ max: 3520, 3416, 2930, 2870, 1740, 1718, 1440, 1380, 1322, 1170, 1080 cm$^{-1}$.

(iv) 3α,7α,12α-Trihydroxy-23-carboxyethylseleno)-24-nor-5β-cholane

Non-radioactive 3α,7α,12α-trihydroxy-23-(β-carboxyethylseleno)-24-nor-5β-cholane was prepared by the method described in 4(iii). The following quantities of reagents were used: 3α-7α,12α-triformoxy-23-iodo-24-nor-5β-cholane, 258.7 mg; sodium borohydride, 61.2 mg; β-selenocyanatopropionic acid, 79.6 mg. Following the final hydrolysis step the product was purified by partition between ether and 5% sodium carbonate solution. The acidic product was isolated and triturated with acetone to give 3α,7α,12α-trihydroxy-23-(β-carboxyethylseleno)-24-nor-5β-cholane (70 mg) as a white powder, m.p. 198°–200°.

IR Spectrum: $\bar{v}$ max: 3520, 3410, 2930, 2870, 1740, 1718, 1440, 1382, 1323, 1170, 1080 cm$^{-1}$.

NMR (220 MHz, CD$_3$OD): τ 5.11 (solvent peak), τ 6.06 (1H, S, C$_{12}$-proton), τ 6.23 (1H, S, C$_7$-proton), τ 6.67 (1H, m, C$_3$-proton), τ 6.71 (solvent peak), τ 7.30 (4H, S, C$_{25}$+C$_{26}$-protons), τ 7.47 and τ 7.78 (2H, m, C$_{23}$-protons), τ 8.97 (3H, d, C$_{21}$-protons), τ 9.10 (3H, S, C$_{19}$-protons), τ 9.30 (3H, S, C$_{18}$-protons), τ 9.70 (unidentified).

EXAMPLE 5

Preparation of
3α,7α,12α-trihydroxy-20-(carboxy-methylseleno)-5β-pregnane (22-selenacholic acid)

(i) 3α,7α,12α-Triformoxy-Δ²²-24-nor-5β-cholene

Cupric Acetate dihydrate (1.0 g) and pyridine (0.7 ml) were added to benzene (170 ml) and the suspension was dried by azeotropic distillation using a Dean and Stark apparatus. After cooling somewhat, dry lead tetraacetate (20 g) and cholic acid triformate (10.5 g, prepared as described in 4(i) were added and the reaction mixture was stirred and heated under reflux in an atmosphere of dry nitrogen for 1½ hours. It was allowed to cool and was filtered. The filtrate was washed successively with water, 1 M sodium hydroxide solution and finally with water, and was dried over anhydrous sodium sulphate. Evaporation of the solvent and crystallisation of the residue from ethanol gave 3α,7α,12α-triformoxy-Δ²²-24-nor-5β-cholene (4.0 g) m.p. 188°–190°.

IR Spectrum: $\bar{v}$ max: 3077, 2960, 2865, 1725, 1714, 1637, 1468, 1449, 1380, 1180 cm$^{-1}$.

NMR Spectrum: τ 1.83, 1.91, 1.98 (3H, three singlets, 3-, 7- and 12- formate protons), τ 4.4 (1H, m, C$_{22}$-proton), τ 4.77 (1H, S, C$_{12}$-proton), τ 4.97 ) 1H, S, C$_7$-proton), τ 5.16 (1H, d, C$_{23}$-proton (cis)), τ 5.18 (1H, S, C$_{23}$-proton (trans), τ 5.30 (1H, m, C$_3$-proton), τ 9.07 (6H, s+d, C$_{19}$-protons+C$_{21}$-protons), τ 9.24 (3H, S, C$_{18}$-protons), τ 7.75–τ 9.1 (22H, steroid nucleus).

(ii) 3α,7α,12α-Triformoxy-23,24-bisnor-5β-cholanic acid

3α,7α,12α-Triformoxy-Δ²²-24-nor-5β-cholene (2.4 g) was dissolved in 2-methylpropan-2-ol (800 ml) and potassium carbonate (1.41 g) in water (800 ml) was added. Sodium periodate (20.86 g) and potassium permanganate (0.395 g) were dissolved in water (1 liter) and an aliquot (435 ml) was added to the solution of the olefin. The solution was stirred at ambient temperature for 24 hours. Sufficient 40% sodium hydrogen sulphite solution was added to discharge the permanganate colouration, 5% sodium carbonate solution was added to pH 8, and the solution was concentrated at reduced pressure to ca. 250 ml. It was extracted with chloroform (2×100 ml), treated with further 40% sodium hydrogen sulphite and acidified with concentrated hydrochloric acid. The mixture was extracted with chloroform (4×100 ml), and the combined extracts were washed successively with 5% sodium thiosulphate solution and water, and then dried. The solvent was evaporated and 100% formic acid (30 ml) was added to the residue. The solution was stirred and heated at 70°–80° for 6 hours and was allowed to cool. It was poured into water and the precipitate was extracted into chloroform (3×50 ml). The combined organic extracts were washed with water, dried and evaporated. The residue was recrystallised from ethanol to give 3α,7α,12α-triformoxy-23,24-bisnor-5β-cholanic acid (0.8 g) m.p. 165°–170°.

IR Spectrum: $\bar{v}$ max: 3410, 2965, 2940, 2870, 1722, 1450, 1385, 1178, 890 cm$^{-1}$.

NMR Spectrum (220 MHz, CDCl$_3$): τ 1.83, 1.91 and 1.98 (3H, 3 singlets, 3-, 7- and 12-formate protons), τ 4.78 (1H,S,C$_{12}$-proton), τ 4.93 (1H,S,C$_7$-proton), τ 5.30 (1H,m,C$_3$-proton), τ 6.29 (2H,q,C$\underline{H}_2$ of ethanol of crystallisation), τ 7.64 (1H,q,C$_{20}$-proton), τ 8.77 (3H,t,C$\underline{H}_3$ of ethanol of crystallisation), τ 8.88 (3H,d,C$_{21}$-protons), τ 9.05 (3,S,C$_{19}$-protons), τ 9.22 (3H,S,C$_{18}$-protons), τ 7.75–9.05 (19H, steroid nucleus).

(iii) 3α,7α,12α-Triformoxy-20-iodopregnane

3α,7α,12α-Triformoxy-23,24-bisnor-5β-cholanic acid (0.2 g) was converted to 3α,7α,12α-Triformoxy-20-iodopregnane (0.11 g) by the method described in 2(i) m.p. 145°–146.5° (decomp).

IR Spectrum: $\bar{v}$ max: 3405, 2950, 2860, 1713, 1445, 1377, 1180 cm$^{-1}$.

NMR Spectrum (220 MHz, CDCl$_3$): τ 1.81, 1.91 and 1.98 (3H, 3 singlets, 3-, 7- and 12-formate protons), τ 4.75 (1H,S,C$_{12}$-proton), τ 4.93 (1H,S,C$_7$-proton), τ 5.30 (1H,m,C$_3$-proton), τ 5.80 (1H,q,C$_{20}$-proton), τ 8.06 (3H,d,C$_{21}$-protons), τ 9.07 (3H,S,C$_{19}$-protons), τ 9.25 (3H,S,C$_{18}$-protons), τ 7.5–9.0 (19H, steroid nucleus).

(iv) 22-Selenacholic Acid-$^{75}$Se

Red selenium-$^{75}$Se (8.2 mg, 106 mCi/mA) was prepared as described in 2(ii). It was suspended in ethanol (2 ml) and dry nitrogen was bubbled through the solution. The exit gases were passed through a trap containing 5% lead acetate solution. Sodium borohydride (2.7 mg) was added and the suspension was stirred at ambient temperature for 20 minutes. n-Propanol (5 ml) was added and the reaction mixture was heated on a boiling water bath for 20 minutes. 3α,7α,12α-Triformoxy-20-iodopregnane (35 mg) in warm n-propanol (2 ml) was added to the solution of disodium diselenide-$^{75}$Se and the whole was heated on a boiling water bath in an atmosphere of dry nitrogen for 3½ hours. It was allowed to cool; it was evaporated under reduced pressure and the residue was treated with chloroform (5 ml). The solution was filtered and evaporated to dryness leaving the impure dipregnane diselenide-$^{75}$Se (4.2 mCi).

Sodium borohydride (5 mg) was dissolved in ethanol (1 ml), the solution was cooled in ice and ethyl bromoacetate (20 μl) was added. The dipregnane diselenide-$^{75}$Se was dissolved in ethanol (3 ml) and was added dropwise over a period of 10 minutes. The reaction mixture was stirred for 2 hours, acetone (1 ml) was added and the solution was evaporated. Chloroform (3 ml) was added, inorganic salts were removed by filtration, and the solution was treated with sodium hydroxide (100 mg) in water (1 ml). The solution was heated under reflux for 3 hours, cooled and evaporated. The residue was dissolved in water (3 ml) and the solution was acidified with concentrated hydrochloric acid and lyophilized. Acetic acid (3 ml) was added to the residue, the solution was filtered and concentrated to a small bulk. The product was purified by preparative layer chromatography, (Anachem Silica Gel GF, 1 mm; dichloromethane, acetone, acetic acid, 7:2:1). Its location was determined by autoradiography, the band was removed from the plate and the product was extracted into acetic acid and the solvent evaporated to give 22-selenacholic acid-$^{75}$Se (0.8 mCi).

TLC (Merck Kiesgel 60 F$_{254}$):
 (a) Dichloromethane, acetone, acetic acid; (7:2:1)
    Major component Rf 0.22
 (b) Chloroform, methanol; (5:1)
    Major component Rf 0.11

IR Spectrum: $\bar{v}$ max: 3400, 2925, 2780, 1715, 1440, 1375, 1265, 1073, 1040 cm$^{-1}$.

(v) Glyco-22-selenacholic acid-$^{75}$Se

22-Selenacholic-$^{75}$Se (0.40 mCi; 1.9 mg) in acetic acid was evaporated to dryness. Dry ethyl acetate (450 μl)

was added followed by N-ethoxycarbonyl-2-ethoxydihydroquinoline (14.2 mg). Ethyl glycinate hydrochloride (8.0 mg), suspended in dry ethyl acetate (0.6 ml), was treated with triethylamine (8.3 μl); the mixture was stirred for 30 minutes and was added to the solution of 22-selenacholic acid-$^{75}$Se, a further quantity of ethyl acetate (0.4 ml) was used to complete the transfer. The reaction mixture was heated under reflux on a boiling water bath for 6 hours; it was then cooled and evaporated. Chloroform (4 ml) was added to the residue and insoluble material was removed by filtration.

Ethyl 22-selenaglycocholate-$^{75}$Se was purified by preparative layer chromatography (Anachem Silica Gel GF, 1 mm; chloroform, methanol 8:1). The major radioactive band was located by autoradiography, Rf 0.4; it was removed from the plate and extracted into methanol (3×4 ml). The solvent was evaporated, ethanol (4 ml) and 10% potassium carbonate solution (1 ml) were added and the solution was heated under reflux for 1 hour and allowed to stand at room temperature overnight. The solution was acidified with concentrated hydrochloric acid, evaporated to dryness and the product was extracted from the residue by dissolving in ethanol. The solution was filtered and evaporated leaving glyco-22-selenacholic acid-$^{75}$Se (0.21 mCi).

TLC (Merck Kieselgel 60 $F_{254}$; chloroform, methanol 3:1): Major component (ca. 85%) Rf 0.04 (cf 22-Selenacholic acid, Rf 0.31 and glycocholic acid, Rf 0.02, in this system).

EXAMPLE 6

Preparation of
3α-Hydroxy-24-(carboxymethylseleno)-5β-cholane (i) 3α-Acetoxy-25-homo-5β-cholanic acid 3α-Acetoxy-25-homo-5β-cholanic acid was prepared from lithocholic acid using the Arndt-Eistert reaction for lengthening the $C_{17}$ side chain.

(ii) 3α-Acetoxy-24-iodo-5β-cholane

3α-Acetoxy-25-homo-5β-cholanic acid was transformed to 3α-Acetoxy-24-iodo-5β-cholane by the method quoted in 4(ii). The quantities of reagents used were as follows: 3α-acetoxy-25-homo-5β-cholanic acid (1.8 g) in dry carbon tetrachloride (120 ml), lead tetraacetate (2.0 g) and iodine (1.04 g) in carbon tetrachloride (80 ml). The crude product was purified by preparative layer chromatography using five Merck Kieselgel 60 $F_{254}$, 2 mm plates developed in chloroform. The required uv. absorbing band was removed from each plate and the product was isolated by extraction with ether. Evaporation of the solvent and trituration of the residue with ethanol gave 3α-acetoxy-24-iodo-5β-cholane (0.43 g; m.p. 140°–146°) as a white powder.

IR Spectrum: $\bar{\nu}$ max: 2940, 2865, 1738, 1473, 1459, 1383, 1366, 1258, 1028 cm$^{-1}$.

NMR Spectrum (220 MHz, CDCl$_3$): τ 5.19 (1H, m,$C_3$-proton), τ 6.83 (2H,m,$C_{24}$-protons), τ 7.98 (3H,S,acetate protons), τ 9.07 (6H,1s+1d, $C_{19}+C_{21}$-protons), τ 9.36 (3H,S,$C_{18}$-protons), τ 8.0–9.1 (28H, steroid nucleus).

(iii) 3α-Hydroxy-24-(carboxymethylseleno)-5β-cholane-$^{75}$Se

Ethyl selenocyanatoacetate-$^{75}$Se (17 mg, 9.2 mCi) was prepared in the manner previously described (2 (ii) ). It was reacted with sodium borohydride (8.2 mg) in ethanol (2 ml) and 3α-acetoxy-24-iodo-5β-cholane (50 mg) in tetrahydrofuran (3 ml) as described in 2(ii). The intermediate 3α-acetoxy-24-(carboxymethylseleno)-5β-cholane ethyl ester-$^{75}$Se was isolated by preparative layer chromatography (Anachem Silica Gel GF; chloroform). The main radioactive band was located by autoradiography (Rf 0.55); it was removed from the plate and the product was isolated by extraction with ethylacetate (3×4 ml). The solvent was evaporated, ethanol (5 ml) and potassium hydroxide (100 mg) in water (1 ml) were added and the solution was heated under reflux for 3 hours and allowed to cool. The solution was acidified with concentrated hydrochloric acid and evaporated under reduced pressure. Ethanol (1 ml) was added to the residue, the solution was filtered and the product isolated by preparative layer chromatography (Anachem Silica Gel GF; chloroform, methanol; 12:1). The required band (Rf 0.20) was located by autoradiography, it was removed from the plate and the product was isolated by extraction with ethanol. Evaporation of the solvent gave 3α-hydroxy-24-(carboxymethylseleno)-5β-cholane-$^{75}$Se (0.8 mCi).

TLC (Merck Kieselgel 60 $F_{254}$; dichloromethane, methanol-15:1): Major Component (94%) - Rf 0.25, coincided with the non-radioactive standard.

IR Spectrum: $\bar{\nu}$ max: 3400, 2930, 2855, 1700, 1445, 1373, 1105, 1028 cm$^{-1}$.

(iv) 3α-Acetoxy-24-(carboxymethylseleno)-5β-cholane ethyl ester

Non-radioactive 3α-acetoxy-24-(carboxymethylseleno)-5β-cholane ethyl ester (160 mg) was prepared by the method given in 6 (iii) from 3α-acetoxy-24-iodo-5β-cholane (200 mg), sodium borohydride (32 mg) and ethyl selenocyanatoacetate (74.7 mg).

IR Spectrum: $\bar{\nu}$ max: 2925, 2855, 1733, 1445, 1375, 1360, 1238, 1100, 1023 cm$^{-1}$.

NMR Spectrum (220 MHz, CDCl$_3$): τ 5.29 (1H,m,$C_3$-proton), τ 5.83 (2H,q,ethyl CH$_3$), τ 6.86 (2H,S,$C_{26}$-protons), τ 7.98 (3H,S,acetate protons), τ 8.72 (3H,q,ethyl CH$_3$), τ 9.0 (6H,1s+1d, $C_{19}$-protons+$C_{21}$-protons), τ 9.36 (3H,S,$C_{18}$-protons).

(v) 3α-Hydroxy-24-(carboxymethylseleno)-5β-cholane

Hydrolysis of 3α-acetoxy-24-(carboxymethylseleno)-5β-cholane ethyl ester according to the method in 6 (iii) gave 3α-hydroxy-24-(carboxymethylseleno)-5β-cholane m.p. 117°–121° C.

IR Spectrum: $\bar{\nu}$ max: 3440, 2920, 2855, 1705, 1443, 1372, 1270, 1165, 1105, 1026 cm$^{-1}$.

EXAMPLE 7

Preparation of
23-(Carboxymethylseleno)-24-nor-5β-cholane-3,7,12-trione-$^{75}$Se (i) 23-Iodo-24-nor-5β-cholane-3,7,12-trione 5β-Cholanic acid-3,7,12-trione was converted to 23-iodo-24-nor-5β-cholane-3,7,12-trione by the method described in 4 (ii). The quantities of reagents used were as follows: 5β-cholanic acid-3,7,12-trione (2 g) in carbon tetrachloride (200 ml), lead tetraacetate (2.3 g), iodine (1.2 g) in carbon tetrachloride (100 ml). The product was recrystallised successively from ethanol and petrol (60°–80°)-ethyl acetate, m.p. 256°–257° C.

TLC (Merck Kieselgel 60 $F_{254}$, chloroform): Major Component Rf 0.36 (if 5β-cholanic acid-3,7,12-trione, Rf 0.08 in this system).

IR Spectrum: $\bar{\nu}$ max: 2960, 2930, 1727, 1708, 1472, 1438, 1392, 1382, 1304, 1280, 1226 cm$^{-1}$.

(ii) 23-(Carboxymethylseleno)-24-nor-5β-cholane-3,7,12-trione-$^{75}$Se

An ethanolic solution of ethyl selenocyanatoacetate-$^{75}$Se (15.3 mg, 8.8 mCi) was prepared by the method described in 2 (ii); it was added to a solution of sodium borohydride (6.6 mg) in ethanol (1 ml) at 0°. After stirring at 0° for 20 minutes, acetone (1 ml) was added followed by 23-Iodo-24-nor-5β-cholane-3,7,12-trione (39 mg) in tetrahydrofuran (1 ml). The reaction mixture was stirred at ambient temperature for 16 hours. The solution was evaporated, chloroform (2 ml) was added and, after filtration, the solution was concentrated and applied to an Anachem 1 mm silica plate which was developed in chloroform, methanol 20:1. Three main radioactive bands were located by autoradiography (Rfs 0.33, 0.49, 0.69); they were removed separately from the plate and the radioactive component was isolated from each by extraction with ether, ethanol (10:1). An examination of the separated components by thin layer chromatography (Merck Kieselgel 60 F254; chloroform) and by infra-red spectroscopy indicated that component Rf 0.49 was the required 23-(carboxymethylseleno)-24-nor-5β-cholane-3,7,12-trione ethyl ester-$^{75}$Se, component Rf 0.33 was a mixture of two unidentified compounds and component Rf 0.69 was non-steroidal.

23-(Carboxymethylseleno)-24-nor-5β-cholane-3,7,12-trione ethyl ester-$^{75}$Se (2.05 mCi) was dissolved in ethanol (5 ml) and 10% potassium carbonate solution (1 ml) was added. The solution was heated under reflux for 2 hours, cooled and evaporated under reduced pressure. Water (4 ml) was added, some insoluble material was removed by filtration and the solution was acidified with concentrated hydrochloric acid and lyophilized. Chloroform (0.5 ml) was added to the residue and the product was isolated by preparative layer chromatography (Anachem Silica Gel Gf, 1 mm; chloroform, methanol-10:1). The main radioactive band was located by autoradiography (Rf 0.32); it was removed from the plate and the product was isolated by extraction with methanol. Evaporation of the solvent gave 23-(carboxymethylseleno)-24-nor-5β-cholane-3,7,12-trione-$^{75}$Se (1.3 mCi).

TLC (Merck Kieselgel 60 F$_{254}$; chloroform, methanol 20:1): Major component—greater than 95% Rf 0.31.

IR Spectrum: $\bar{\nu}$ max: 2965, 2895, 1717, 1475, 1428, 1395, 1275, 1118 cm$^{-1}$.

EXAMPLE 8

Preparation of 3α,12α-dihydroxy-23-(carboxymethyltelluro)-24-nor-5β-cholane (i) 3α,12α-Diformoxy-23-Iodo-24-nor-5β-cholane 3α,12α-Diformoxy-5β-cholanic acid was prepared from deoxycholic acid (25 g) and 100% formic acid ) 100 ml) by the method described in 4 (i). The product was recrystallised from ethanol giving colourless crystals (17.5 g), m.p. 197°–199° C.

3α,12α-Diformoxy-5β-cholanic acid (4 g) was converted to 3α,12α-Diformoxy-23-iodo-24-nor-5β-cholane by the method previously described (4 (ii)) using lead tetraacetate (4.0 g) and iodine (1.9 g). The crude product was crystallised from ethanol giving colourless crystals m.p. 123°–125° C. (3.1 g).

IR Spectrum: $\bar{\nu}$ max: 2940, 2865, 1723, 1447, 1383, 1205, 1190, 1180 cm$^{-1}$.

NMR Spectrum (220 MHz, CDCl$_3$): τ 1.89 and 1.98 (2H, two singlets, 3- and 12-formate protons), τ 4.75 (1H,S,C$_{12}$-proton), τ 5.19 (1H,m,C$_3$-proton), τ 6.71 (1H,m,C$_{23}$-proton), τ 6.96 (1H,q,C$_{23}$-proton), τ 9.06 (3H,S,C$_{19}$-protons), τ 9.16 (3H,d,C$_{21}$-protons), τ 9.22 (3H,S,C$_{18}$-protons), τ 7.95–9.15 (24H, steroid nucleus).

(ii) 3α,12α-dihydroxy-23-(carboxymethyltelluro)-24-nor-5β-cholane-$^{123m}$Te $^{123m}$-Tellurium (6 mg, 5 mCi) was dissolved in concentrated hydrochloric acid (2 ml) and hydrogen peroxide (100 vol. 2 drops). Tellurium oxide (23 mg inactive) was added and the resulting solution was diluted with water (32 ml). Tellurium metal was precipitated using sulphur dioxide gas, was washed twice with water and then with ethanol, and was finally dried in vacuum.

To tellurium metal (24.6 mg, 5 mCi) in a reaction vessel containing 15 ml of liquid ammonia was added Sodium (4.4 mg), the vessel being connected to a vacuum manifold and vented to the atmosphere via a carbosorb/charcoal trap. The reaction mixture was stirred for 5 minutes to obtain disodium ditelluride-$^{123m}$Te and then iodoacetic acid (35.8 mg) was added. The ammonia was allowed to evaporate, and traces of volatile matter were removed under reduced pressure.

The residue was redissolved in ethanol (20 ml) and dimethylformamide (10 ml) and stirred under an atmosphere of nitrogen. Sodium hydroxide (0.1 g) in water (3 ml) and dithiothreitol (50 mg) in water (2 ml) were added. After 20 minutes 3α,12α-diformoxy-23-iodo-24-nor-5β-cholane in dimethyl formamide (2 ml), was added. The reaction mixture was stirred at 60° for 1 hour and at room temperature overnight. The solvents were evaporated in vacus, and the residue dissolved in chloroform (2 ml) and then purified by preparative layer chromatography on cellulose (Avicel F Butanol, water, acetic acid 60:25:15). The active band, Rf 0.9–0.96 as observed by autoradiography, was removed from the plate, and extracted into chloroform. Evaporation of the chloroform yielded a residue of 350 μCi (7%).

TLC: Cellulose; (butanol, water, acetic acid 60:25:15). Major component (>95%) - Rf 0.95.

IR Spectrum: $\bar{\nu}$ max: 2950, 2920, 2860, 1725, 1450, 1385, 1125, 1070, 1035, 875, 790, 740 cm$^{-1}$.

(iii) 3α,12α-dihydroxy-23-(carboxymethyltelluro)-24-nor-5β-cholane

This was prepared as in 8 (ii). Tellurium (59 mg), Sodium (11.5 mg), iodoacetic acid (84 mg), Sodium hydroxide (0.2 g) dithiothreitol (100 mg) 3α,12α-diformoxy-23-iodo-24-nor-5β-cholane (190 mg) were used.

Yield 30 mg (16%).

IR Spectrum: $\bar{\nu}$ max: 2940, 2860, 1725, 1450, 1385, 1130, 1070, 875, 790 cm$^{-1}$.

NMR Spectrum (CD$_3$OD)(220 MHz): τ 6.05 (1H,S,C$_{12}$-proton), τ 8.97 (3H,d,C$_{21}$-protons), τ 9.08 (3H,S,C$_{19}$-protons), τ 9.28 (3H,S,C$_{18}$-protons).

What we claim is:

1. A method for investigating body function of a mammal, comprising introducing a γ-emitting radioactive Se or Te labelled derivative of a bile acid or a bile salt comprising an amino acid conjugate of a bile acid or a metabolic precursor thereof in to the live mammal, and after the elapse of a suitable period of time determining the distribution of the radioactivity.

2. A method as claimed in claim 1 for investigating bowel function of a mammal, comprising orally administering the γ-emitting radioactive Se or Te labelled derivative of a bile acid or salt or metabolic precursor thereof to the live mammal, and after the elapse of a suitable period of time determining the distribution of the radioactivity.

3. A method as claimed in claim 2, wherein the distribution of the radioactivity is determined by body counting.

4. A method as claimed in claim 2, wherein the distribution of the radioactivity is determined by faecal counting.

5. A method as claimed in claim 1 for investigating liver function of a mammal, comprising intravenously administering the γ-emitting radioactive Se or Te labelled derivative of a bile acid or salt or metabolic precursor thereof to the live mammal, and after the elapse of a suitable period of time determining the distribution of the radioactivity.

6. A method as claimed in claim 1, wherein the bile acid or salt or metabolic precursor thereof is labelled with selenium-75 or tellurium-123 m.

7. A method as claimed in claim 1, wherein the bile acid or salt is labelled at the 19-position.

8. A method as claimed in claim 1, wherein the bile acid or salt is labelled in the C-17 side chain.

9. A method as claimed in claim 8, wherein the labelled bile acid is 3α, 12α-dihydroxy-22-(carboxymethyl-[$^{75}$Se] seleno)-23,24-bisnor-5β-cholane.

* * * * *